United States Patent [19]

Becker et al.

[11] 4,247,559

[45] Jan. 27, 1981

[54] N-SUBSTITUTED MALEIMIDES IN LIQUID CONCENTRATES

[75] Inventors: Frank C. Becker, Gurnee; Jorge P. Li, Libertyville, both of Ill.

[73] Assignee: Abbott Laboratories, North Chicago, Ill.

[21] Appl. No.: 23,070

[22] Filed: Mar. 23, 1979

[51] Int. Cl.$^3$ .................. C07D 207/452; A61K 31/40
[52] U.S. Cl. ............................ 424/274; 260/326.5 SF
[58] Field of Search ................ 260/326.5 SF; 424/274

[56] References Cited

U.S. PATENT DOCUMENTS 3,821,247  6/1974  Sturm et al. ................ 260/326.5 SF

FOREIGN PATENT DOCUMENTS 2703266 10/1978 Fed. Rep. of Germany ... 260/326.5 SF

*Primary Examiner*—Jose Tovar
*Attorney, Agent, or Firm*—Paul D. Burgauer; Robert L. Niblack

[57] ABSTRACT

It has been found that N-phenylmaleimides carrying certain haloalkylsulfonyl substituents are excellent industrial biocides.

7 Claims, No Drawings

N-SUBSTITUTED MALEIMIDES IN LIQUID CONCENTRATES

DETAILED DESCRIPTION OF THE INVENTION

Many industrially used liquid, emulsions, solutions or dispersions requiring extended storage or use, i.e. paints, leather treatment liquids, coolants, metal cutting fluids, etc. are subject to bacterial or fungal deterioration and must be protected against such micro-organisms. Many biocides have been suggested in the past, a number of which are no longer acceptable because of environmental control regulations, and others are not sufficiently effective against the most common fungi.

A new class of industrial biocides, which is very effective against bacteria and fungi, has now been found. This class is represented by the formula

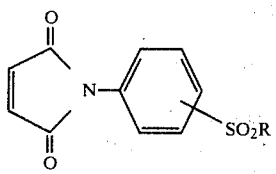

wherein R is $-CH_2hal$ or $-CH_{13\ hal2}$. These halomethyl N-maleimidylphenyl sulfones act as industrial biocides, inhibiting the growth of the most common industrial fungi and bacteria at concentrations of 0.1% and below.

The compounds of the present invention can easily be prepared by condensing maleic anhydride with an aniline carrying the above defined substituent $RSO_2-$. The aniline derivatives of this nature are prepared, in turn, by the method of Goldberg and Besly, J. Chem. Soc. 1945, p. 566. Various acidic reaction media can be used for the above condensation with maleic anhydride, preferably glacial acetic acid or sulfonic acid. The ratio of the reactants is preferably chosen in a 1:1 molar ratio, although a 20% by weight excess of either reactant does not adversely affect the yield. The condensation usually takes only about one hour at reflux temperature of the reaction medium, but for best yields, a period of up to 4 hours is recommended. When temperatures below reflux or below 100° C. are chosen for this condensation, periods of 1–10 hours are indicated, in accordance with well-known principles of thermodynamics.

In order to illustrate the present invention, reference is made to the following examples which, however, are not intended to limit the invention in any respect.

EXAMPLE 1

To a solution of 5.1 g. p-(chloromethylsulfonyl)aniline in 50 ml. of glacial acetic acid is added 2.7 g of freshly pulverized maleic anhydride and the resulting mixture is stirred and heated to reflux for 2.5 hours. After cooling, the mixture is filtered and the filtrate is evaporated in vacuo to produce 2 g. of N-[p-(chloromethylsulfonyl)phenyl]maleimide. This material is purified first by passing it through a silica gel column, using dichloromethane as the solvent, and subsequently by recyrstallization from ethyl acetate/ethanol, producing silky, white needles, m.p. 180°–1° C.

By replacing the above p-(chloromethylsulfonyl)aniline with the m-(chloromethylsulfonyl)- or o-(chloromethylsulfonyl)anilines, the corresponding N-[m-(chloromethylsulfonyl)phenyl]- or N-[o-(chloromethylsulfonyl)phenyl]maleimides are obtained in similar yields.

EXAMPLE 2

A mixture of 6 g. of p-(dichloromethylsulfonyl)aniline and 3 g. of maleic anhydride in 50 ml. of glacial acetic acid is stirred and heated to reflux for 3 hours. The solvent is then removed in vacuo and the residue is triturated with water to produce 7.5 g. of N-[p-(dichloromethylsulfonyl)phenyl]maleimide; m.p. 151°–2° C. after a silica gel passage as in Example 1 and recrystallization from ethanol.

EXAMPLE 3

A mixture of 8.1 g. of maleic anhydride and 31.7 g. of p-(diiodomethylsulfonyl)aniline in 160 ml. of glacial acetic acid is treated in the fashion of Example 2 to produce crude N-[p-(diiodomethylsulfonyl)phenyl]maleimide. This material is washed with water, airdried, and recrystallized from acetone to a pale, crystalline powder, m.p. 217° C.

EXAMPLE 4

A mixture of 63.7 g. of N-[p-(iodomethylsulfonyl)phenyl]acetamide and 360 ml. of 5.5 N sulfuric acid is stirred and heated at reflux until all of the solid dissolves. After cooling, the crude, solid product separates; it is collected, washed with cold water and airdried. After crystallization from methanol, 26 g. of p-(iodomethylsulfonyl)aniline is obtained; m.p. 169.5°–72° C.

To 4.23 g. of this material in 250 ml. of glacial acetic acid is added 1.1 g. of freshly pulverized maleic anhydride. Following the treatment of Example 2, 3.45 g. of N-[p-iodomethylsulfonyl)phenyl]maleimide is obtained. Upon crystallization once from DMF-water and once from acetone, one obtains the pure product; m.p. 204°–5° C.

When this reaction is repeated with N-[m-(diiodomethylsulfonyl)phenyl]acetamide as the starting material, N-[m-diiodomethylsulfonyl)phenyl]maleimide is obtained.

In similar fashion, N-[p-fluoromethylsulfonyl)phenyl]maleimide is prepared from p-(fluoromethylsulfonyl)aniline (Yagupol'skii et al, Ukr. Khim.Zh., 38, 1034 of 1972)and p-(bromomethylsulfonyl)aniline (Stevenson et al, U.S. Pat. No. 2,937,970) converts to N-[bromomethylsulfonyl)phenyl]maleimide.

EXAMPLE 5

The new compounds are dissolved in DMF at a concentration of 50 mg/ml. and diluted with water to the appropriate concentration to be added to a nutrient broth in test tubes. The challenge mixture contains $1 \times 10^6$ colony-forming units each of *Aerobacter aerogenes*, *Pseudomonoas* Sp., *Bacillus subtilus* and *Bacillus megaterium*. Following inoculation, the tubes are incubated 48 hours at 37° C., subcultured to fresh nutrient broth and incubated 24 hours longer. The results are recorded as presence or absence of turbidity, turbidity indicating growth of the inoculum due to inactivity of the biocide at the concentration used in the broth.

In a related test, the above biocide solutions are added to agar plates at various concentrations and the plates are then inoculated with 1 ml. of a broth containing 10,000 units each of *A. niger* and *P. funiculosum*. The plates are then incubated at 30° C. for two weeks, and growth of the fungi is visually inspected to establish the minimum inhibitory concentration (MIC).

The following table shows the result of the above two tests:

| Compound | Antibacterial MIC | Antifungal MIC |
| --- | --- | --- |
| R=p-CH$_2$Cl | 1000 | 1000 |
| R=p-CH$_2$I | — | 100 |
| R=p-CHCl$_2$ | 1000 | 1000 |
| R=p-CHI$_2$ | 1000 | 1000 |
| R=CCL$_3$ | inactive | inactive |

From the above it will be seen that mono- or dihalogenation of the sulfonylmethyl group is critical for biocidal activity, as the trihalogenated analog is ineffective.

The current compounds easily solubilize in a number of solvents that are often used as carriers for additives for industrial fluids. Concentrates for easy further dilution can be made in a number of solvents industrially acceptable at the low concentrations required at the ultimate dilution, e.g. ethylene glycol, tetrahydrofuran, dioxane, DMF, DMAc, N-methylpyrrolidine or mixtures thereof, and other solvents may be used to make easily dilutable dispersions, e.g. aqueous dispersions. Solutions or dispersions of this nature, containing 5-50% by weight of the new biocide are particularly suitable for easy storing and shipping and being readily dilutable for use in cutting fluids, cooling water, etc. or dispersible in agricultural mixtures, paints, coating formulations or the like.

We claim:

1. A liquid concentrate for addition to industrial solutions, emulsions, liquids or dispersions to protect such industrial fluids from deterioration by micro-organisms, containing a compound of the formula

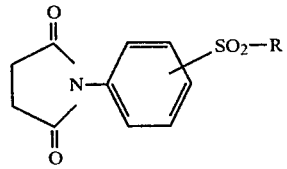

wherein R is CH$_2$—hal or CH—hal$_2$, wherein hal stands for iodine or chlorine, together with an industrially acceptable diluent.

2. A concentrate according to claim 1 wherein said —SO$_2$R substituent is in the p-position.

3. A concentrate according to claim 2 wherein said diluent essentially is DMF.

4. The concentrate of claim 2 wherein R is CH$_2$I.

5. The concentrate of claim 2 wherein R is CHI$_2$.

6. The concentrate of claim 2 wherein R is CH$_2$Cl.

7. The concentrate of claim 2 wherein R is CHCl$_2$.

* * * * *